DEFENSIVE PUBLICATION

UNITED STATES PATENT AND TRADEMARK OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent and Trademark Office makes no assertion as to the novelty of the disclosed subject matter.

PUBLISHED DECEMBER 2, 1975

941 O.G. 8

T941,017

BENZAZOCINES AS LOCAL ANESTHETICS

John Edgar Giering, West Bloomfield, N.Y., John Alan Beech, Talahassee, Fla., and George Camougis, Worcester, Mass., assignors to Pennwalt Corporation, Philadelphia, Pa.

Continuation of application Ser. No. 427,271, Dec. 21, 1973, which is a continuation of application Ser. No. 14,211, Feb. 24, 1970, both now abandoned. This application Nov. 6, 1974, Ser. No. 521,325

Int. Cls. A61k *31/135, 31/445*

U.S. Cl. 424—267

No Drawing. 19 Pages Specification

The use of pentazocine, cyclazocine and similar 1,2,3,4, 5,6 - hexahydro - 2,6 - methano - 3 - benzazocine derivatives as local anesthetics, and compositions containing said compounds and epinephrine.